United States Patent
Hess et al.

[11] Patent Number: 5,817,040
[45] Date of Patent: Oct. 6, 1998

[54] KNEE AND ELBOW ORTHOSIS

[75] Inventors: Clarence E. Hess, Safety Harbor, Fla.; Harold T. Varn, Lawrenceville, Ga.

[73] Assignee: Restorative Care of America Incorporated, Clearwater, Fla.

[21] Appl. No.: 990,178

[22] Filed: Dec. 12, 1997

Related U.S. Application Data

[63] Continuation of Ser. No. 519,117, Aug. 24, 1995, abandoned.

[51] Int. Cl.$^6$ ...................................................... A61F 5/00
[52] U.S. Cl. .................................................. 602/16; 602/26
[58] Field of Search ..................... 602/5, 16, 20, 602/23, 26

[56] References Cited

U.S. PATENT DOCUMENTS

| | | | |
|---|---|---|---|
| Re. 34,818 | 1/1995 | Daneman et al. | 602/26 |
| 4,088,130 | 5/1978 | Applegate | 602/26 X |
| 4,340,041 | 7/1982 | Frank | 602/26 |
| 4,503,846 | 3/1985 | Martin | 602/26 X |
| 4,531,515 | 7/1985 | Rolfes | 602/16 |
| 4,817,588 | 4/1989 | Bledsoe | 602/16 |
| 4,887,590 | 12/1989 | Logue et al. | 602/26 |
| 4,941,462 | 7/1990 | Lindberg | 602/26 X |
| 4,982,732 | 1/1991 | Morris | 602/26 X |
| 5,000,169 | 3/1991 | Swicegood et al. | 602/16 |
| 5,052,379 | 10/1991 | Airy et al. | 602/16 |
| 5,062,858 | 11/1991 | Broeck et al. | 602/16 X |
| 5,292,303 | 3/1994 | Bastyr et al. | 602/26 X |
| 5,316,547 | 5/1994 | Gildersleeve | 602/16 X |
| 5,409,449 | 4/1995 | Nebolon | 602/16 |
| 5,443,444 | 8/1995 | Pruyssers | 602/16 X |
| 5,460,599 | 10/1995 | Davis et al. | 602/16 |

*Primary Examiner*—Linda C. Dvorak
*Attorney, Agent, or Firm*—Zarley,McKee,Thomite, Voorhess & Sease

[57] ABSTRACT

A knee and elbow orthosis has a frame comprised of an upper pair of arms and a lower pair of arms with a pivotal connection therebetween. U-shaped brackets are attached to the outer ends of the upper pair of arms and the lower pair of arms to provide for connection to the limbs of a patient adjacent the joint being treated. The pivotal connection between the upper and lower pair of arms includes stop elements for variably limiting the range of pivotal motion between the upper and lower pair of arms. A lock element operatively connected to both pair of arms can selectively lock the arms in a fixed orientation with respect to each other.

1 Claim, 5 Drawing Sheets

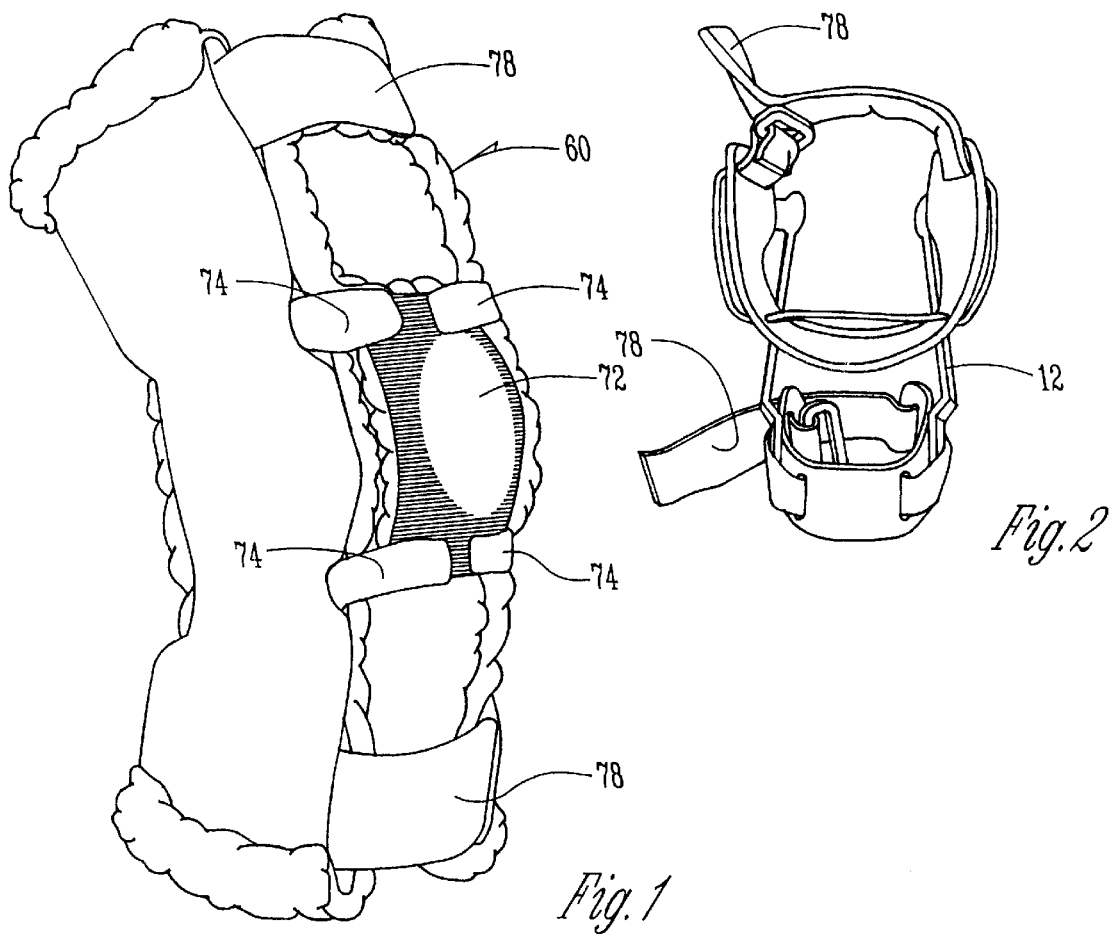
Fig. 1
Fig. 2
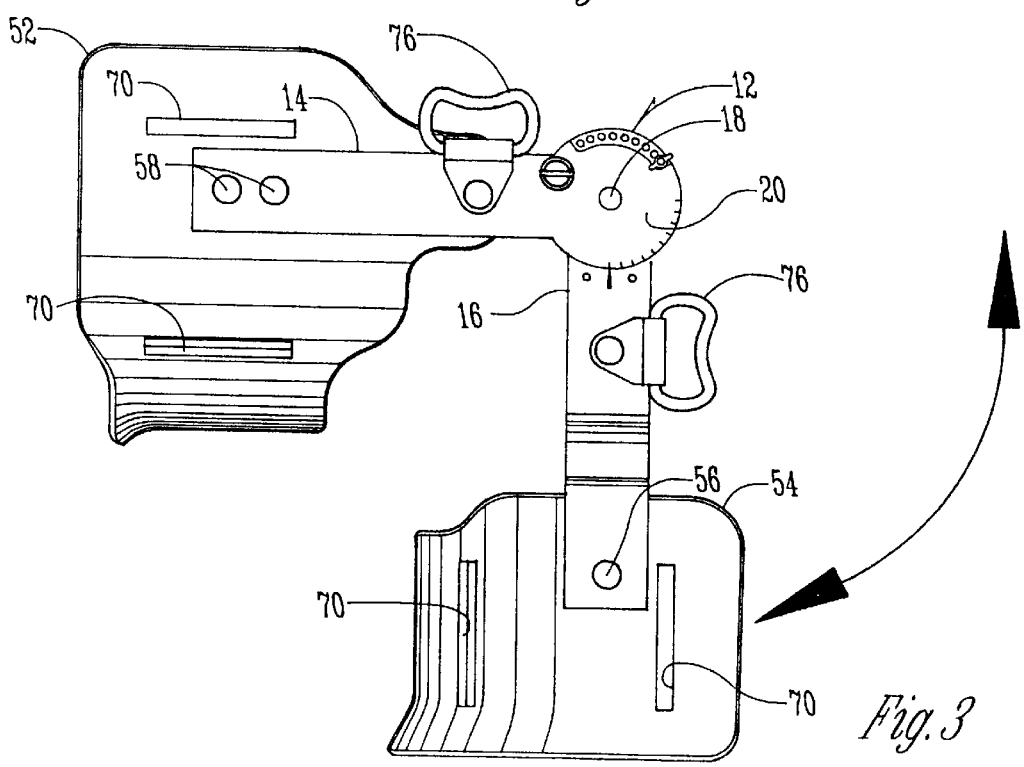
Fig. 3

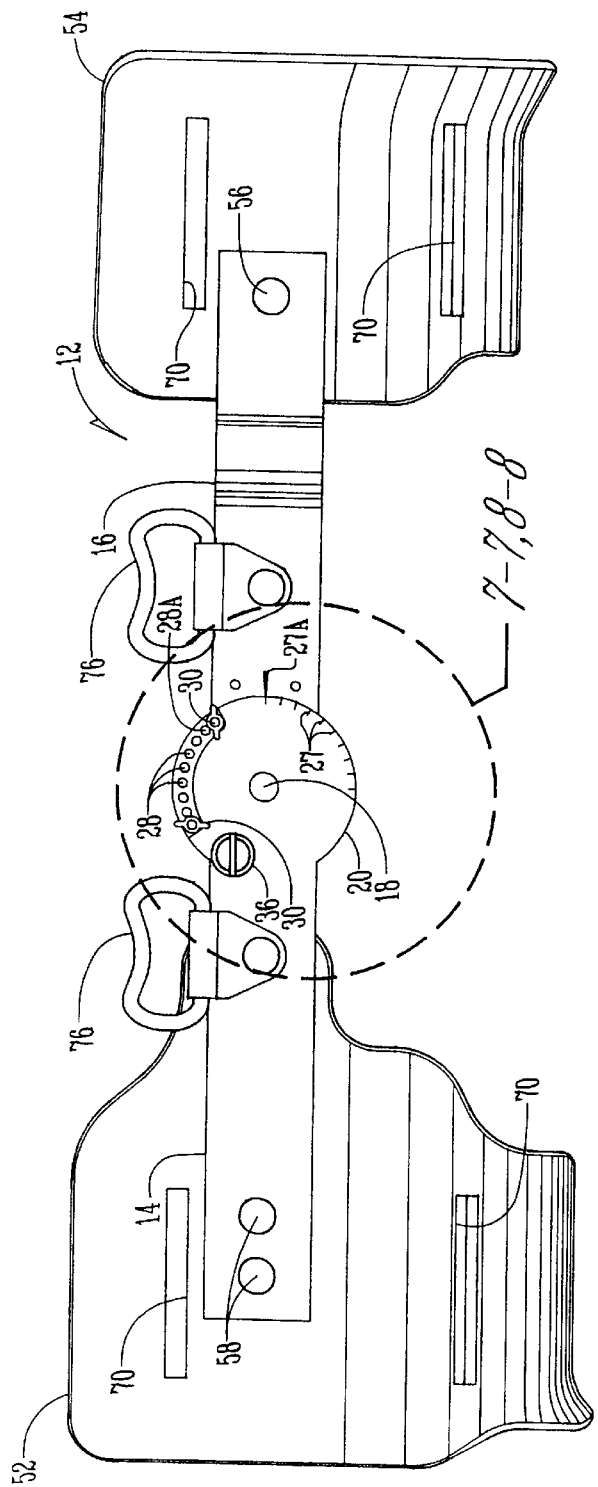
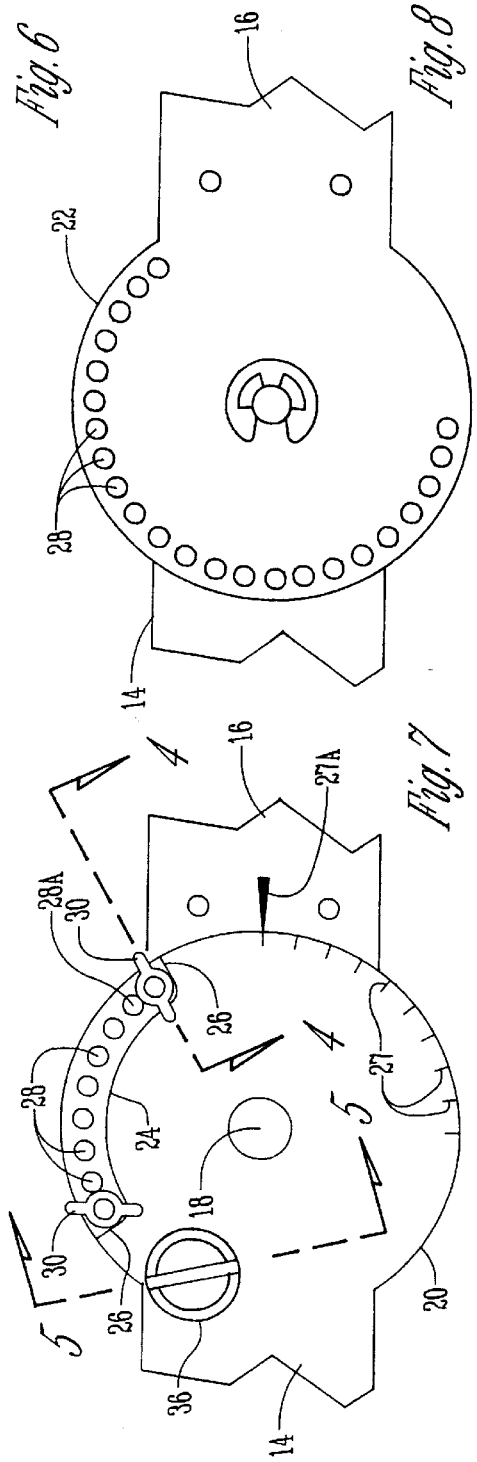

KNEE AND ELBOW ORTHOSIS

This is a continuation of Ser. No. 08/519,117 filed on Aug. 24, 1995, now abandoned.

BACKGROUND OF THE INVENTION

The prior art does not provide a device or a system that is fully adequate for rehabilitation of patients who suffer from joint stiffness (i.e., knee and elbow stiffness) and soft tissue contractures.

It is therefore a principal object of this invention to provide a knee and elbow orthosis that is suitable and effective for providing rehabilitation for joint stiffness and soft tissue contractures.

A further object of this invention is to provide a knee and elbow orthosis which will offer adjustable positioning capabilities to allow gradual joint extension for a wide variety of patients.

It is a still further object of this invention to provide a knee and elbow orthosis that will provide a range of motion for the joints, but which can also provide a static, or serial splinting setting for positive lock immobilization.

A still further object of this invention is to provide a knee and elbow orthosis which will allow a protected range of motion to meet the needs of individual patients.

A still further object of the invention is to provide a knee and elbow orthosis which includes padding or liners which add comfort to the patient and which are easily cleaned or replaced.

These and other objects will be apparent to those skilled in the art.

SUMMARY OF THE INVENTION

The knee and elbow orthosis of this invention has an orthosis frame comprising an upper pair of arms and a lower pair of arms which are pivotally connected together. Each pair of arms has a receptacle for an upper and lower limb, respectively, for attachment to the limb of a patient above and below, or on either side, of the joint that is being treated.

The pivotal connection between the upper and lower arms comprises a stop assembly for variably limiting the range of pivotal motion between the upper and lower arms, and a locking means is included to fix the pivotal position between the upper and lower arms when desired.

BRIEF DESCRIPTION OF THE DRAWINGS

FIG. 1 is a frontal perspective view of the device of this invention;

FIG. 2 is a smaller scale top plan view of the device of FIG. 1 with the padding or liner material removed therefrom;

FIG. 3 is a large scale side elevational view of the orthosis frame of this invention;

FIG. 6 is a side elevational view of the device of FIG. 3 in an extended and longitudinally aligned position;

FIG. 7 is a large scale elevational view taken on line 7—7 of FIG. 6;

FIG. 8 is a view similar to that of FIG. 7 taken in the locality of lines 8—8 of FIG. 6, but shows the inner end of a lower arm which is partially hidden in both FIGS. 6 and 7;

DESCRIPTION OF THE PREFERRED EMBODIMENT

Figure 4:
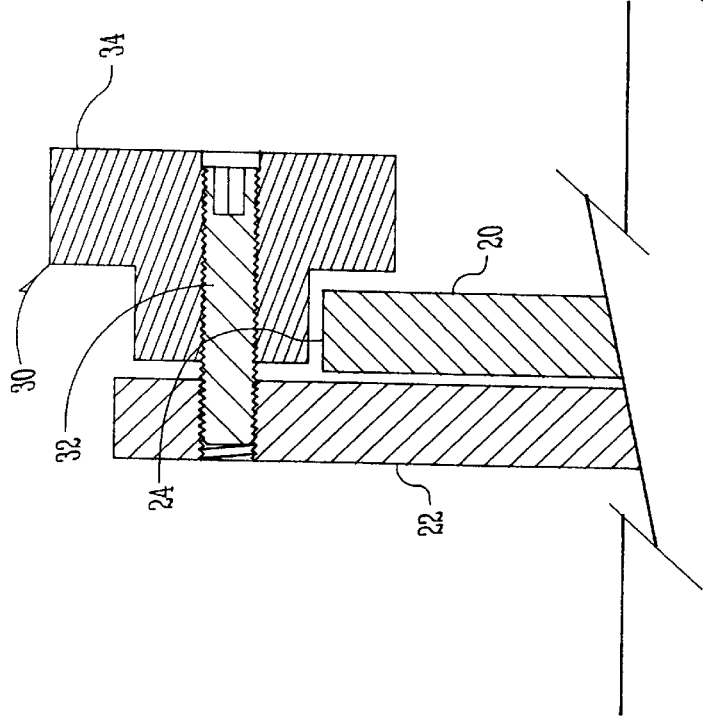
FIG. 4 is a large scale sectional view taken on line 4—4 of FIG. 7.

The invention disclosed herein is suitable for use on either the knee or the elbow of a patient requiring treatment. However, the form of the invention used for the elbow is of a smaller size than the size used for treating a patient's knee. Nevertheless, the principal of this invention is equally applicable to either a knee or an elbow orthosis.

The assembled orthosis of this invention is designated by the numeral 10 as best shown in FIG. 1. With reference to FIG. 6, the numeral 12 designates the orthosis frame which is comprised generally of a pair of upper arms 14 and a pair of lower arms 16 which are pivotally secured together by pins 18. The numeral 20 designates circular disks on the inner or lower ends of upper arms 14. Similarly, the numeral 22 designates circular disks that are on the upper or inner ends of lower arms 16. The disks 20 are superimposed on the disks 22, and pins 18 serve to permit the disks as well as the arms to pivot with respect to each other. Disk 20 has an arcuate slot 24 therein (FIG. 7) with the slot having opposite ends 26. A plurality of indicia marks 27 are located on a portion of the periphery of disks 20. Indicia marks represent degrees and there should be sufficient indicia marks to show the angular disposition of the disks with respect to base indicia mark 27A in a range of 0° to 90°. Base indicia mark 27A is located on the inner end of arm 16 as best shown in FIG. 6.

As best shown in FIG. 8, disk 22 has a plurality of threaded apertures 28 located along over one-half of its periphery. It should be noted that the peripheral distance taken up by apertures 28 on disk 22 exceeds the peripheral distance of slot 24 in disk 20. Stop screws 30 (FIG. 4 and FIG. 7) have a threaded shaft 32 and a solid wing nut 34 on one end thereof. The threaded shafts 32 are adapted to be threadably engaged within the threaded apertures 28 on disk 22. As will be discussed hereafter, the location of stop screws 30 in selected apertures 28 abut the ends 26 of slot 24 to define the range of pivotal motion that the arms 14 and 16 can have with respect to each other.

Figure 5:
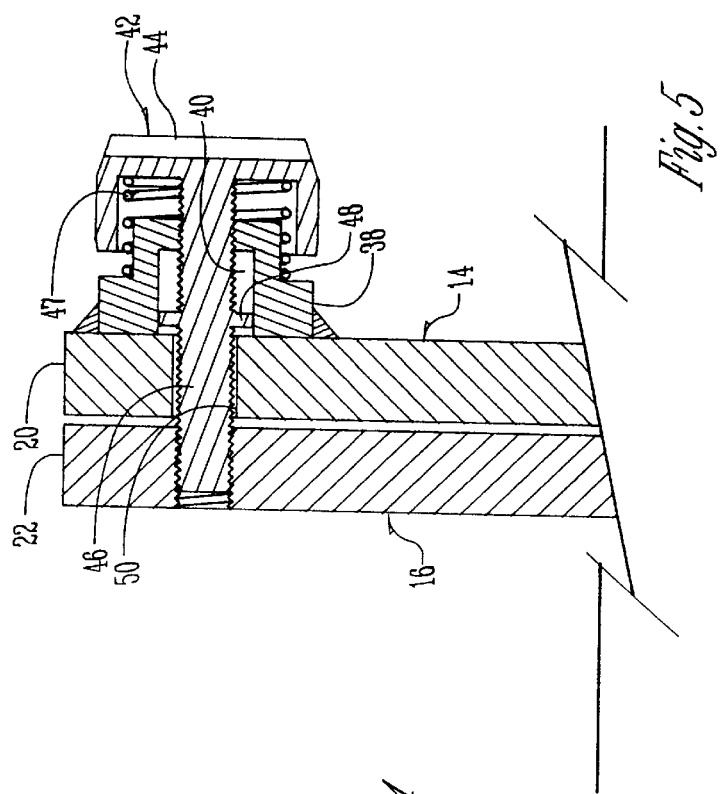
FIG. 5 is a large scale sectional view taken on line 5—5 of FIG. 7.

A lock element 36 (FIGS. 5 and 7) is mounted on disk 20 and its base 38 is rigidly secured thereto by any suitable means. The base has an internal bore 40. A screw 42 has a hollow top 44 and a threaded stud 46 which extends downwardly through a suitable aperture in the hollow top 44 of the screw. A stop ring 48 extends around stud 46 at its mid point. The portion of stud 46 opposite to the hollow top 44 slidably extends through bore 50 in disk 20. The end of stud 46 opposite to hollow top 44 is adapted to be threadably received within one of the threaded apertures 28 in disk 22. (See. FIG. 5).

A U-shaped upper limb bracket 52 is secured between upper arms 14, and a U-shaped lower limb bracket 54 is secured between the lower ends of lower arm 16. Rivets 56 pivotally secure the arms 16 to bracket 54 and rivets 58 rigidly secure the bracket 52 to arms 14.

Figure 9:
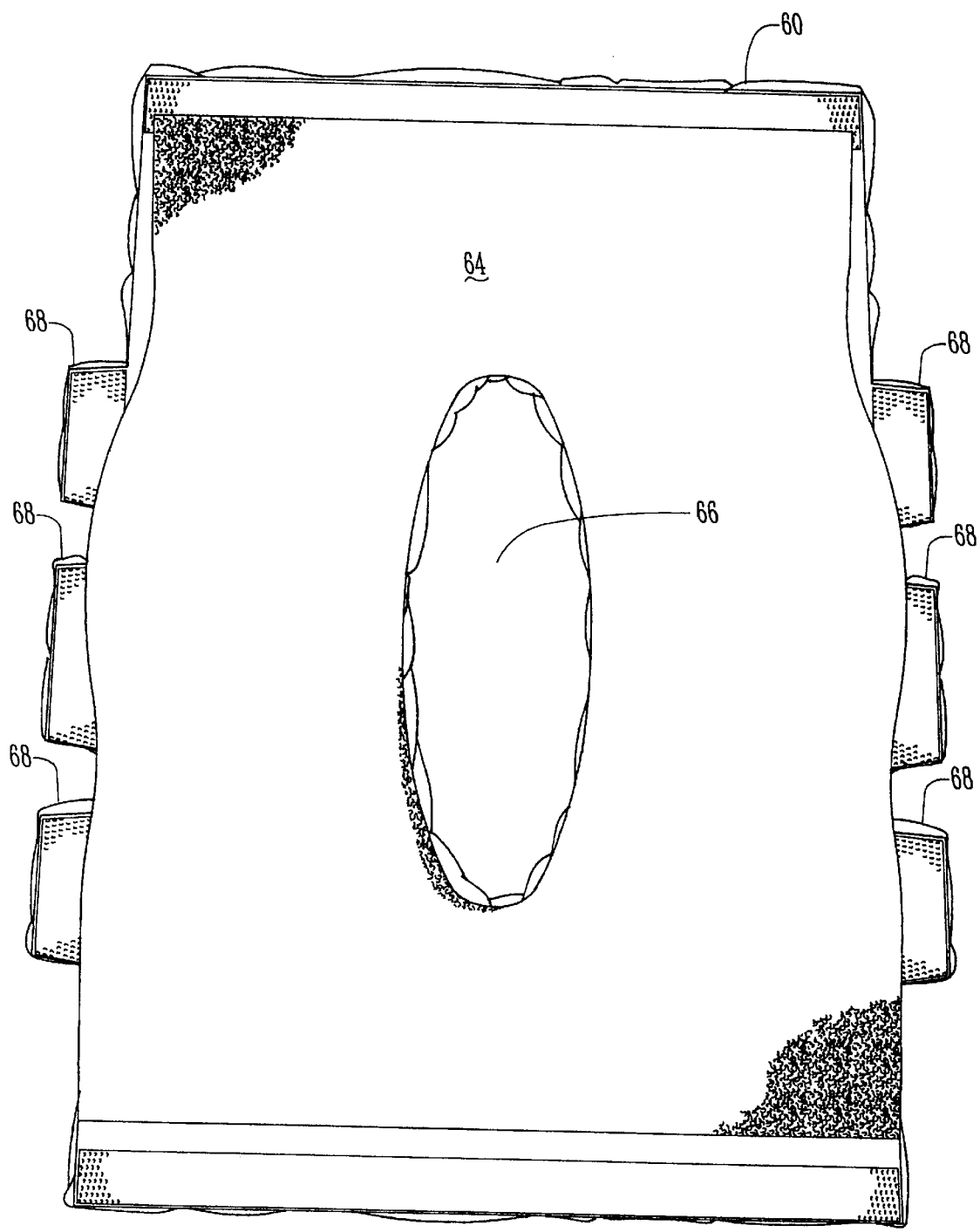
FIG. 9 is a top plan view of the principal liner for the device of this invention.
Figure 10:
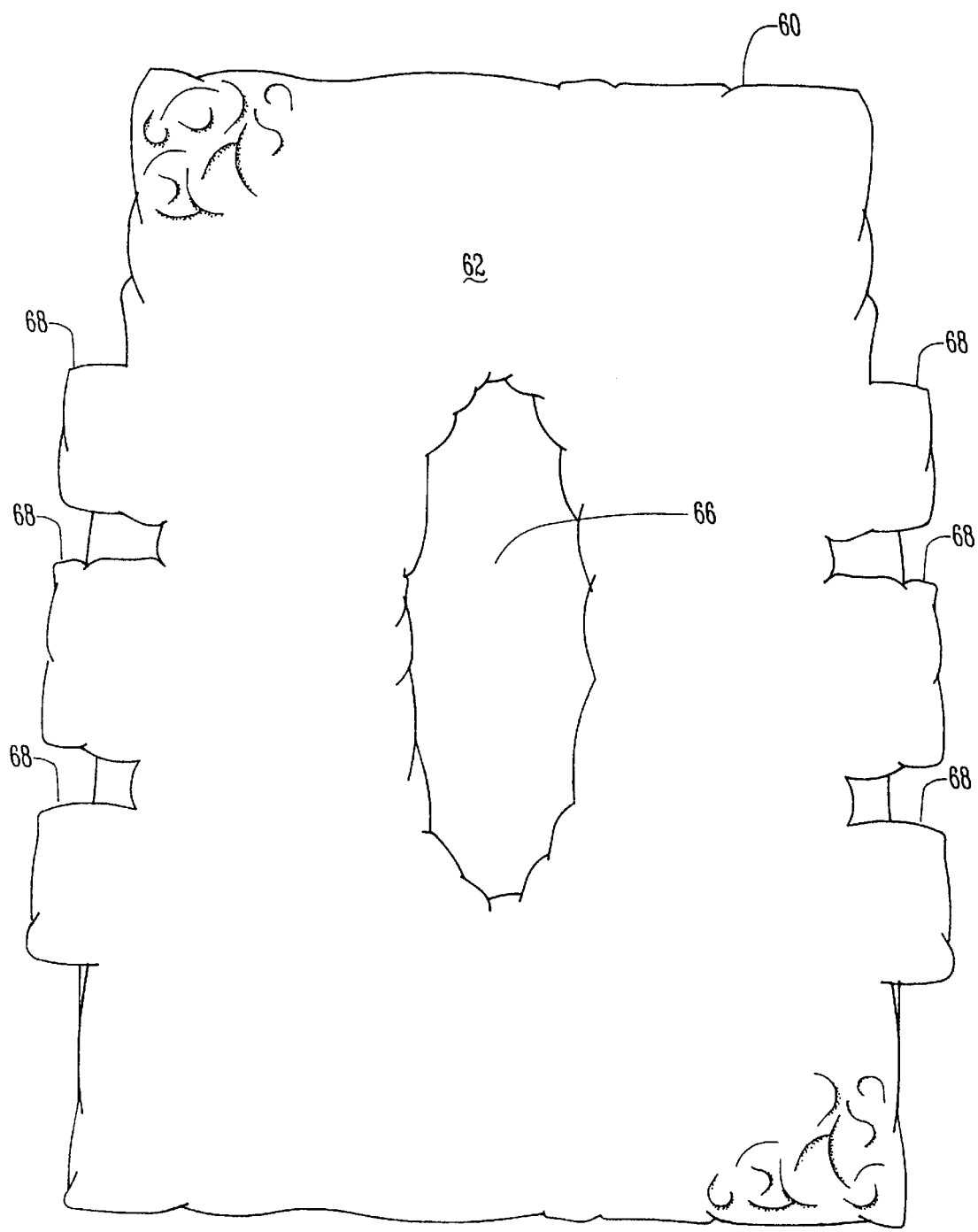
FIG. 10 is a bottom plan view of the structure shown in FIG. 9.

A rectangular pad 60 (FIGS. 9 and 10) has a soft inner layer 62 and is comprised of Kodel® or the like to provide padding for the patient. The outer layer 64 is of more durable material and is preferably comprised of Ortho-Wick™ which is a foam liner that absorbs perspiration away from the patient's skin to promote good skin integrity. A center opening 66 appears in both of the layers 62 and 64 so as to provide freedom for movement of the joint to a bent rather than an extended position. Velcro-type fasteners 68 are mounted on the peripheral sides of the pad or liner 60 to detachably secure the layers 62 and 64 together.

As best seen in FIGS. 3 and 6, a plurality of elongated slits 70 appear in brackets 52 and 54. A knee or elbow cup or pad 72 has four straps 74 extending therefrom which are adapted to be secured to buckles 76 which are secured to the arms 14 and 16 (FIGS. 3 and 6). Straps 78 are threaded through the pad 60 and through the slits 70 in the brackets 52 and 54 to secure the orthosis 10 to the leg or arm of the patient. The straps 78 have appropriate fasteners on the ends thereof to facilitate the securement of the straps together.

In operation, the pad 50 is folded about its longitudinal axis and placed over the orthosis frame 12 when the frame is in the position of FIG. 6. This is normally done after the pad 72 has been secured to the buckles 76 as described heretofore. Again, the pad 50 is affixed to the brackets 52 and 54 by means of the straps 76.

When it is desired to give the patient an initial small increment of motion of the joint that is being treated, the lock element 36 is removed from any threaded contact within the aperture 28 of disk 22. With reference to FIG. 5, this is accomplished by screwing member 42 out of aperture 28. As soon as the threaded connection between threaded stud 46 is removed from aperture 28, the spring 47 withdraws the end of thread stud 46 into the bore 50 so that the disk 20 is free to rotate with respect to the disk 22. Stated differently, the release of screw 42 in the manner just described permits the upper arms 14 to be pivoted with respect to the arms 16.

The foregoing discussion assumes that none of the stop screws 30 are threadably inserted into any of the threaded bores 28.

Having released the screw 42 in the manner described, and with reference to FIG. 6, one of the stop screws 30, for example, would be moved into the aperture 28A if a range of motion of approximately 10° was desired. The other stop screw 30 would be placed in the position of the left-hand stop screw 30 as shown in FIG. 6. This would allow the lower pair of arms 16 to be moved in a clockwise direction with respect to the arms 14 as shown in FIG. 6 and would permit the patient to have movement of the knee or elbow joint through this range of 10°

As progress of the patient progressed, the right-hand stop screw 30 in FIG. 8 could be moved to successive apertures 28 to increase the angular range of motion.

Whenever it is desired to stabilize the patient's joint, the lock screw 42 could be actuated by screwing it into a suitable aperture 28 in-disk 22 to lock the arms 14 and 16 in a fixed position.

The Velcro fasteners 68 permit the easy disassembly of the pad 60 for cleaning or replacement purposes. The knee or elbow pad 72 can be easily disassembled from the buckles 76 for cleaning or replacement.

It is therefore seen that the device of this invention will permit the joint of a patient to have a reasonable range of motion depending upon the condition of the joint being treated. It is seen that all of the objects of this invention can therefore be achieved by the use of this invention.

What is claimed is:

1. A knee and elbow orthosis, comprising:

an orthosis frame comprising an upper pair of arms, a corresponding lower pair of arms, each arm of the upper pair of arms being pivotally connected respectively with one arm of the lower pair of arms to form respective pivotal connections, first means on the upper ends of said upper pair of arms for connection to an upper limb above a limb joint, second means on the lower ends of said lower pair of arms for connection to a lower limb below a limb joint, one of said pivotal connections comprising stop means for variably limiting the range of pivotal motion between said upper and lower pair of arms, said stop means includes an axially spring loaded plunger in one of said pair of pivotally connected arms positioned opposite to a plurality of apertures in said other pivotally connected arms with each aperture being adapted to receive said plunger, said stop means has a stop element to limit or stop the range of pivotal motion between said upper and lower pair of arms, said stop means further comprises a circular disk on the lower ends of said upper arms and the upper ends of said lower arms, respectively; said disks being superimposed over each other and pivotally connected in pairs at their respective centers, one of each pair of disks having an arcuate peripheral slot positioned opposite to a plurality of apertures in the other of said disks whereupon a pair of stop elements located within said apertures will impinge upon one of the ends of said slot to limit the range of pivotal motion between said upper and lower arms, said plurality of apertures being located adjacent a first portion of the peripheries of said circular disks, and visible indicia means comprising radially spaced radial marks adjacent a second portion of the peripheries of said circular disk opposite a base indicia mark on one of said arms with the radial space between said radial marks equating the space between said apertures.

* * * * *